United States Patent
Kobayashi

[19]

[11] Patent Number: 5,935,087
[45] Date of Patent: Aug. 10, 1999

[54] SITTING-POSTURE BODY ANTEFLEXION MEASURING DEVICE

[75] Inventor: Kando Kobayashi, Machida, Japan

[73] Assignee: University of Tokyo, Tokyo, Japan

[21] Appl. No.: 09/135,894

[22] Filed: Aug. 18, 1998

[30] Foreign Application Priority Data

Aug. 18, 1997 [JP] Japan .................................. 9-221389

[51] Int. Cl.$^6$ .................................................. A61B 5/103
[52] U.S. Cl. ........................................... 600/595; 482/132
[58] Field of Search ........................... 482/95, 131, 132; 600/587, 594, 595

[56] References Cited

U.S. PATENT DOCUMENTS

| | | |
|---|---|---|
| 3,101,944 | 8/1963 | Cencig ..................................... 482/132 |
| 3,925,901 | 12/1975 | McCormick ............................... 33/759 |
| 5,401,224 | 3/1995 | Tsuchiya et al. ....................... 600/595 |
| 5,435,315 | 7/1995 | McPhee et al. .......................... 600/587 |
| 5,518,483 | 5/1996 | Oswald .................................. 482/131 |
| 5,567,202 | 10/1996 | Hager ..................................... 482/131 |

*Primary Examiner*—Cary O'Connor
*Assistant Examiner*—Pamela L. Wingood
*Attorney, Agent, or Firm*—Knobbe, Martens, Olson & Bear, LLP

[57] ABSTRACT

The disclosed measuring device includes a base plate with a scale for measuring a sitting-posture body anteflexion of a subject, and a back plate for supporting the back of the subject is connected to the base plate so that it can assume an upright posture relative to the base plate. A movable table is guided along the scale on the base plate toward and away from the back plate. The table has a cursor for reading the movement distance of the table from a reference point of the scale.

6 Claims, 8 Drawing Sheets

FIG_4

SITTING-POSTURE BODY ANTEFLEXION MEASURING DEVICE

BACKGROUND OF THE INVENTION

1. Field of the Invention

The present invention relates to a body anteflexion measuring device and, more particularly, to a sitting-posture body anteflexion measuring device which can be easily and safely used by people of various ages for performing a body anteflexion without undue physical burden.

2. Description of Related Art

Typically, body anteflexion is performed to ascertain the flexibility of a human body as one item of physical fitness test associated, e.g., with the prevention of lumbago. The body anteflexion test is generally classified into two categories; i.e., a standing-posture body anteflexion test in which measurement is made in the standing posture of the subject, and a sitting-posture body anteflexion test in which measurement is made in the sitting posture of the subject with the knees unrestrained.

Conventional devices for measuring the body anteflexion are disclosed, for example, in a Japanese publication "Physical Fitness Science", No. 18, p. 121, Sep. 1996. Thus, there is known a standing-posture body anteflexion measuring device which includes a stand for placing both feet of the subject thereon, and a scale in combination with a cursor which can be engaged by the finger tips of the subject so that the cursor is moved by the finger tips in the standing posture of the subject and the movement distance of the cursor along the scale is read. There is also known a sitting-posture body anteflexion measuring device of movable cursor type, in which the fingers of both hands of the subject are brought into tight contact with each other in a sitting posture of the subject whose knees are unrestrained, and the cursor is moved by the finger tips along a predetermined path and the movement distance of the cursor from a reference point is read. This type of measuring device may include a handle which can be rotated for adjusting the height of the cursor, or a seat which can be moved horizontally in combination with the cursor of a fixed height.

It is a recent trend in various countries to adopt a sitting-posture body anteflexion test method. The procedure for performing a sitting-posture body anteflexion is essentially based upon traditional standing-posture body anteflexion included as one of the sports test items specified, for example, by Japanese Ministry of Education. Thus, the body anteflexion motion in a sitting-posture of the subject is performed with both legs being stretched or unrestrained. A procedure for the sitting-posture body anteflexion test has been proposed by Wells et al. in 1952, in which the body anteflexion motion is performed by using a measuring stand with a height of about 30 cm, and adopting a sitting posture on a floor so that the bottom faces of the feet are in contact with the vertical front surface of the stand. In this instance, the front edge of the stand is used as the measurement reference point (zero point) and measurement is made of the horizontal distance between the reference point and the position which is reached by the finger tips of both hands as a result of the maximum anteflexion motion and which can be maintained for about two seconds.

The traditional procedure for the sitting-posture body anteflexion test has been modified in order to minimize undesirable fluctuation due to the different leg length of the subjects, and the modified procedures are known as Werner's method (1992) or Minkler's method (1994). In such modified procedures, a sitting posture is first adopted, with the back of the subject kept in contact with a wall surface, and the upper limbs and the fingers stretched forward at the same height as that of the measuring stand. The position of the finger tips of both hands in such a sitting posture of the subject is taken as the measurement reference point. The body anteflexion is then performed to measure the horizontal distance between the reference point and the position which is reached by the finger tips of both hands as a result of the maximum anteflexion motion and which can be maintained for about two seconds.

With any of the above-mentioned conventional measuring methods, not only the posture of the subject is still unstable, but it is also difficult to achieve a satisfactory repeatability of the measurement. Moreover, by adopting the predetermined, rather unnatural posture of the subject during the measurement, the muscles and/or tendons on the back side of knees are unduly stretched thereby causing a physical pain.

SUMMARY OF THE INVENTION

It is therefore a primary object of the present invention to provide an improved device for measuring a sitting-posture body anteflexion, which is easy and safe to use, and essentially free from the above-mentioned problems of the conventional methods.

According to the present invention, there is provided a sitting-posture anteflexion measuring device which comprises: a base plate provided with a scale for measuring anteflexion of a subject, said scale extending in a longitudinal direction of the base plate and having a predetermined reference point; a back plate having a lower end connected to one end of said base plate, said back plate being capable of assuming an upright posture relative to the base plate; and a table which is movable in the longitudinal direction of the base plate toward and away from the back plate, said table having a cursor which is movable along the scale for reading the movement distance of the cursor as measured from said reference point.

With the measuring device according to the present invention, the body anteflexion can be performed in a state in which a sitting posture of the subject is adopted with the back in contact with the back plate, and both hands are placed on the movable table so that the subject can assume a natural posture and the motion of the subject during the anteflexion can be stabilized. Also, since both legs of the subject during the measurement are unrestrained, the subject is essentially free from a physical pain which could not be eliminated when the muscles and/or tendons on the back side of the knee are unduly stretched.

The device according to the present invention may further comprise side stays for retaining the back plate in the upright posture relative to the base plate. In this instance, it is preferred that the stays are detachably connected to the back plate and the base plate.

The back plate may be pivotally connected to the base plate so that it can be folded over the base plate.

The table may comprise a table top member, a plurality of legs connected to the table top member, and means for adjusting the height of said table top member relative to said base plate. In this instance, the legs of the table may be pivotally connected to the table top member.

The base plate may have a pair of longitudinal guide tracks along both side edges of the base plate, for guiding a caster provided for each leg of the table.

BRIEF DESCRIPTION OF THE DRAWINGS

The present invention will be explained below in further detail, with reference to a preferred embodiment shown in the accompanying drawings, in which.

DESCRIPTION OF THE PREFERRED EMBODIMENT

Referring now to FIGS. 1 through 4, there is shown a sitting-posture body anteflexion measuring device according to one preferred embodiment of the present invention. The device includes a base plate 1 which is provided with a scale S for measuring the body anteflexion. The scale S extends in the longitudinal direction of the base plate 1. The base plate 1 has one end to which a lower end of a back plate 2 is pivotally connected so that the back plate 2 can assume an upright posture relative to the base plate 1. Preferably, side stays 3 are detachably provided on both sides of the device, for retaining the back plate 2 in the upright posture relative to the base plate 1. A movable table 4 is arranged on the base plate 1 so that the table 4 can be moved in the longitudinal direction of the base plate 1, toward and away from the back plate 2.

Figure 1:
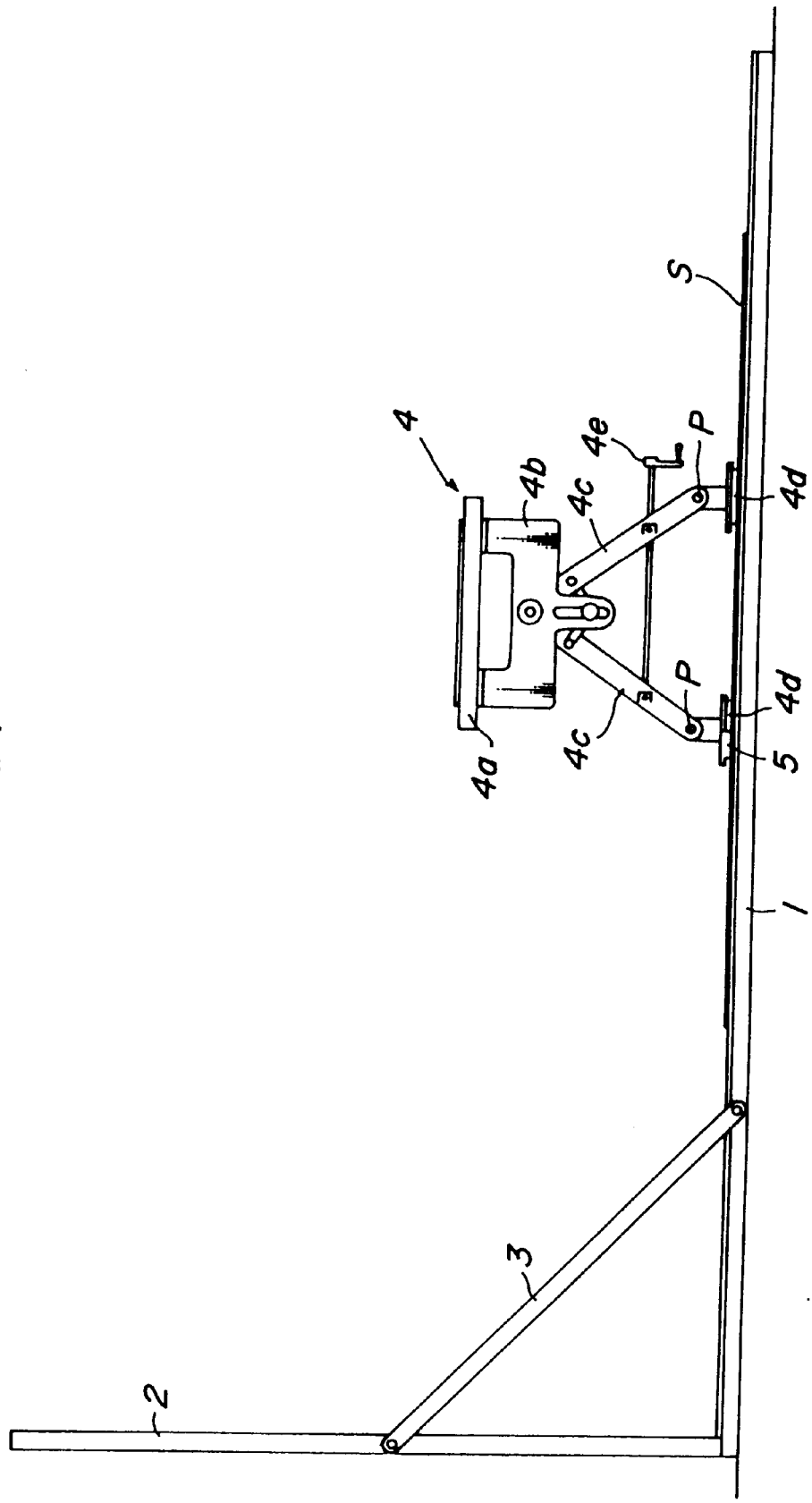
FIG. 1 is a side view of the measuring device in accordance with a preferred embodiment of the present invention.
Figure 2:
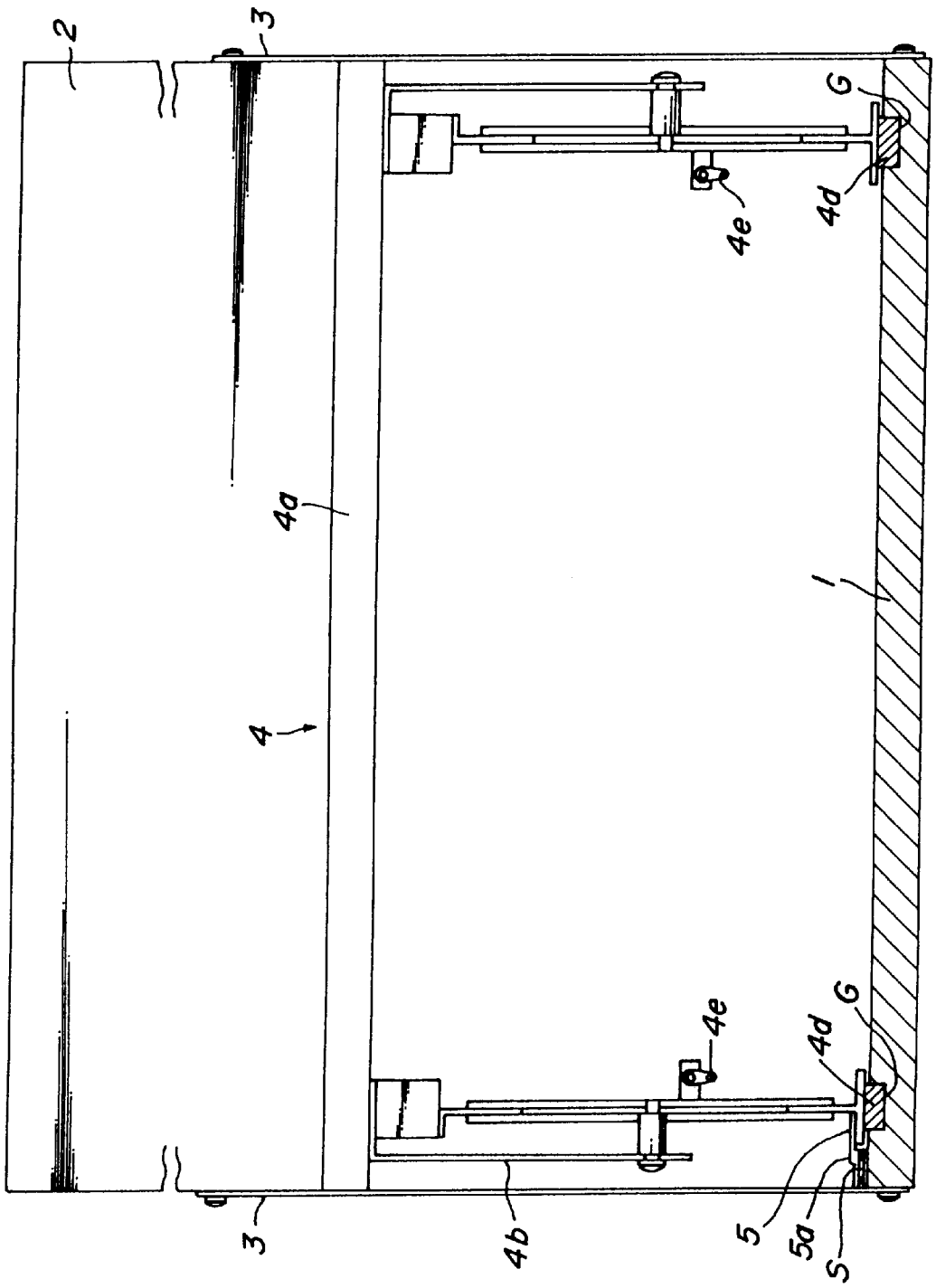
FIG. 2 is a front view of the device shown in FIG. 1.
Figure 3:
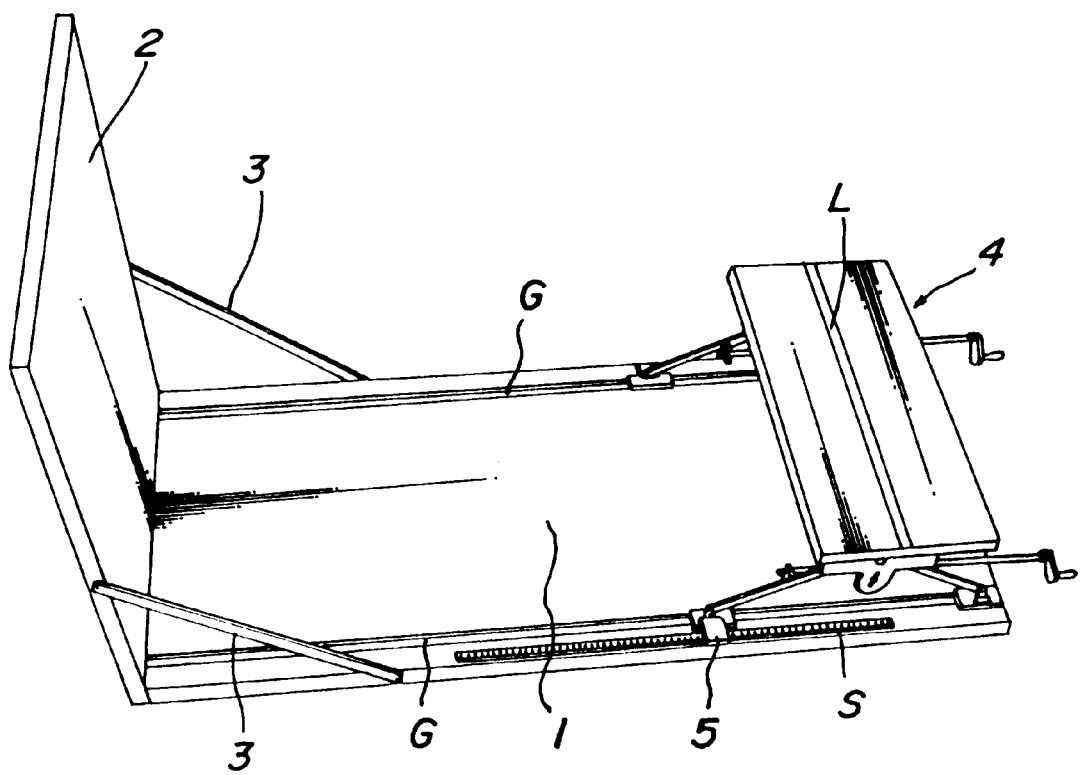
FIGS. 3 and 4 are perspective views of the device shown in FIG. 1.
Figure 4:
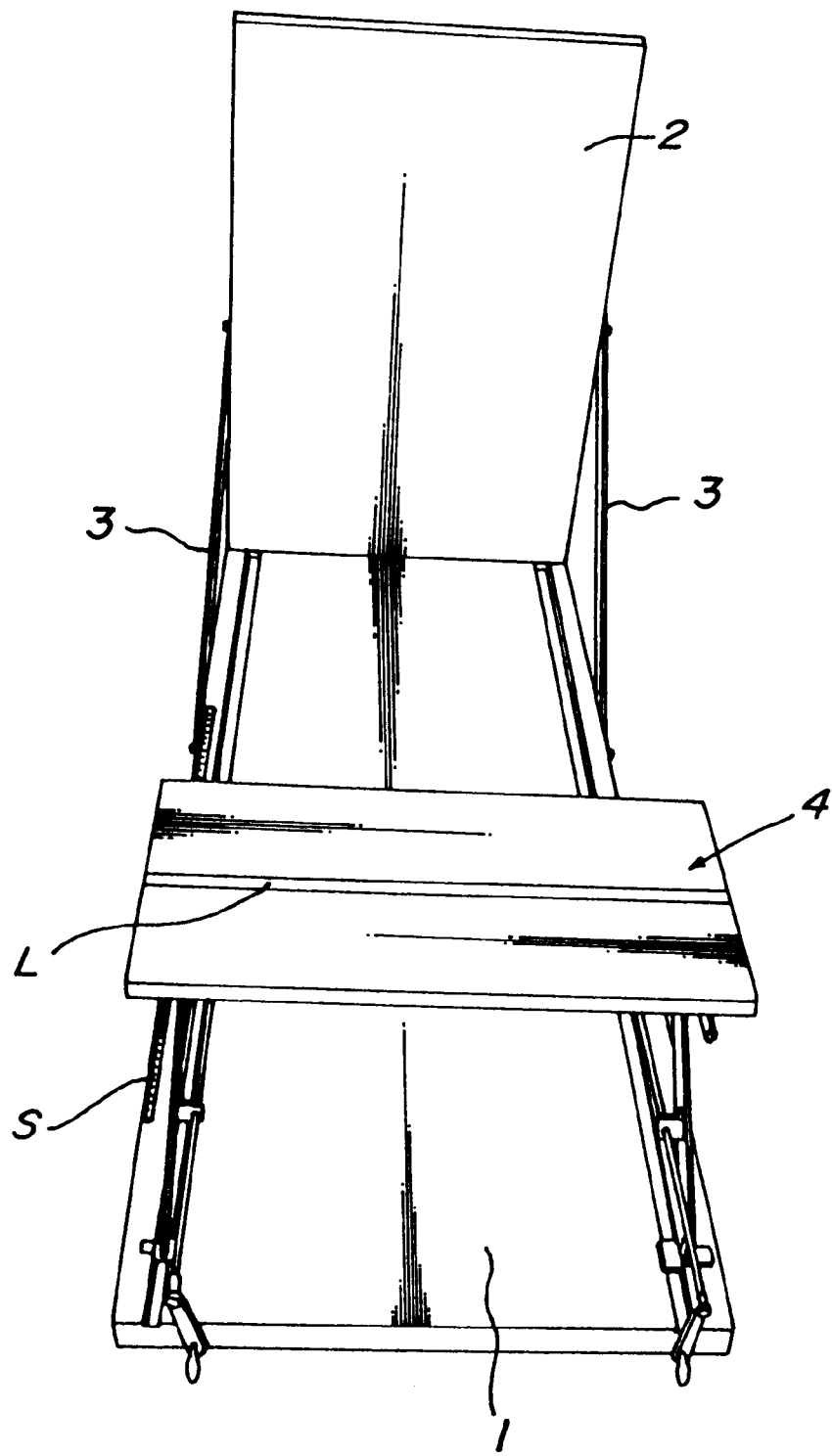

More particularly, the table 4 includes a table top member 4a having a reference line L inscribed thereon, as shown in FIGS. 3 and 4, on which both hands of a subject can be placed so that the finger tips of both hands of the subject can always be positioned at the same location. A parallel motion mechanism 4b serves to support the table top member 4a thereon, for maintaining the table top member in a horizontal plane. The table 4 further includes a plurality of legs 4c which are pivotally connected to the parallel motion mechanism 4b, and casters 4d which are pivotally connected to the lower ends of the legs 4c, as shown at P in FIG. 1. The legs 4c are associated with adjusting handles 4e on both sides of the device, which can be manually rotated for adjusting the height of the table top member 4a relative to the base member, by changing the angles formed between mutually opposite legs 4d.

The table 4 is so arranged that the casters 4d are engaged into, and guided by grooves G which are formed in the base plate 1 in parallel with the scale S, such that the table 4 in its entirety can be moved freely along the groove G. A cursor 5 is connected to one of the casters 4c which is adjacent to the scale S, so that the cursor 5 is moved along the scale S upon the movement of the table 4 in the longitudinal direction of the base plate 1. The cursor 5 makes it possible to read the movement distance of the table 4 from the reference point (i.e., the initial point) of the scale S.

The manner of performing a measurement of the sitting-posture body anteflexion of a subject, by using the measuring device as described above, will be described below.

Figure 5:
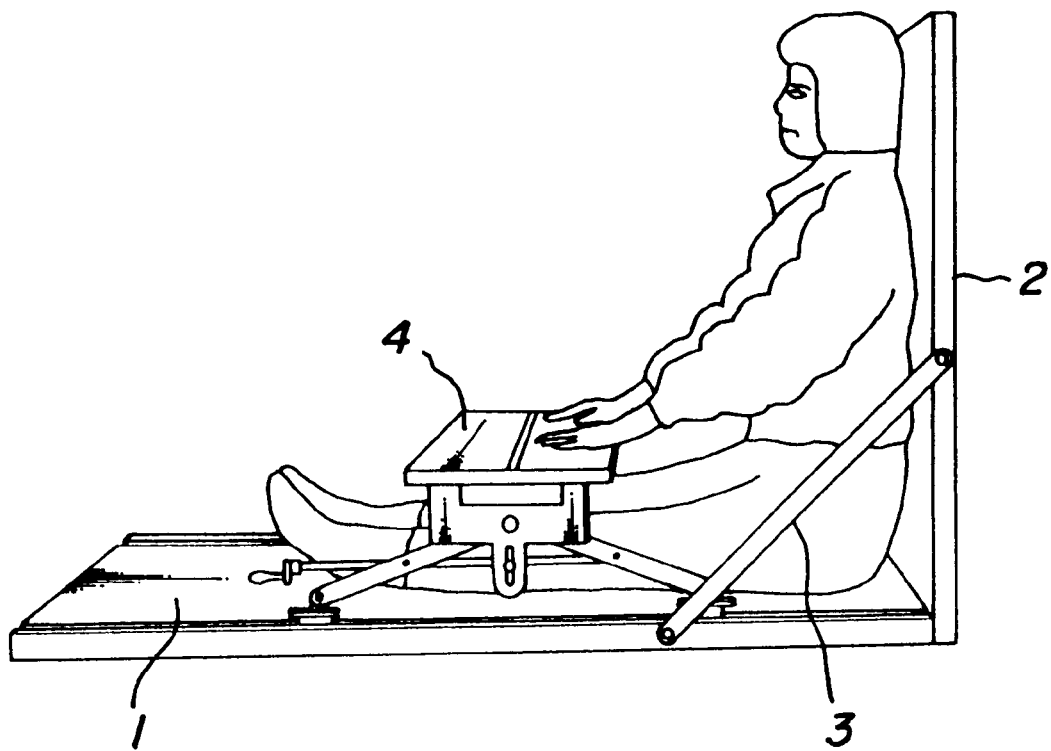
FIG. 5 is a view showing a state before performing a body anteflexion.

First of all, as shown in FIG. 5, the subject assumes a sitting posture on the base plate 1, putting the back on the back plate 2 of the device and both legs below the table top member 4a such that the legs of the subject are stretched in the longitudinal direction of the base plate 1. On this occasion, it should be ensured that the hip and the back of the subject are in close contact with the back plate 2. Also, both hands of the subject are placed on the table top member 4a, with the palms being directed downward and spaced from each other substantially at an interval of about the breadth of the shoulders, and the finger tips of both hands being positioned on the reference line L (FIGS. 3 and 4).

Then, warming-up body anteflexion motions are performed for a couple of times such that the table 4 is moved back and forth with both knees of the subject stretched. At this time, the ankles of the subject are left unrestrained so that they assume a natural state.

Figure 7A:
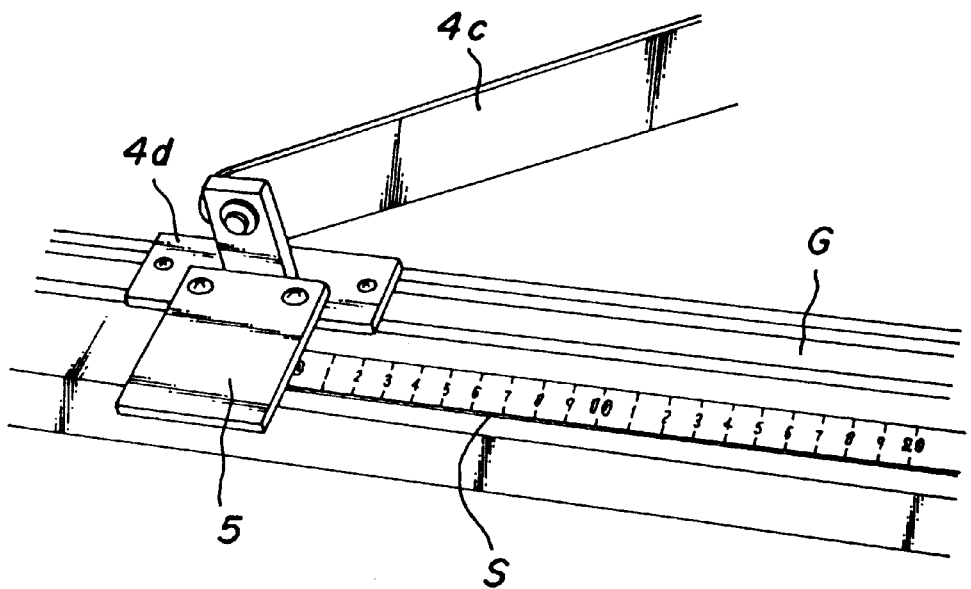
FIGS. 7A and 7B are views showing a cursor before and after it has been moved by the body anteflexion.

In the next place, the elbows of the subject are stretched in a posture in which the backbone is stretched while the hip and back are in contact with the back plate 2, to determine the reference point (i.e., the initial point) of the table 4 along the scale S, as shown in FIG. 7a. Also, the height of the table top member 4a is adjusted by turning the handles 4e such that the angle between the back plate 2 of the device and the arm (i.e., the angle of the armpit) becomes approximately 50 to 55 degrees.

Figure 6:
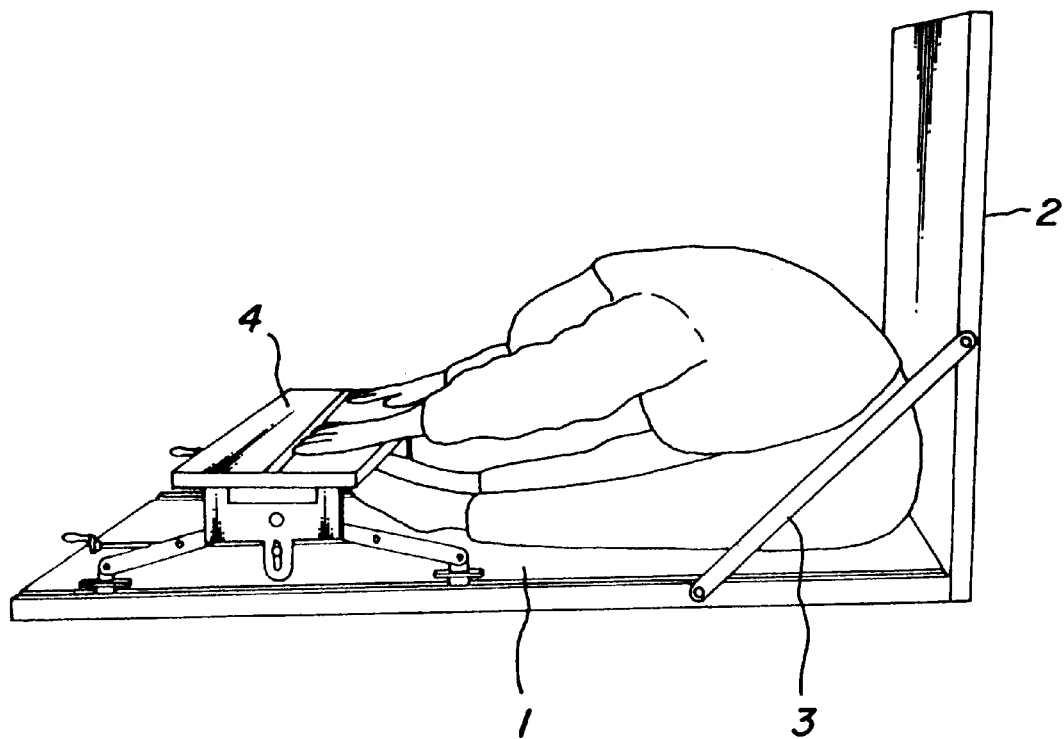
FIG. 6 is a view showing a state during the body anteflexion.
Figure 7B:
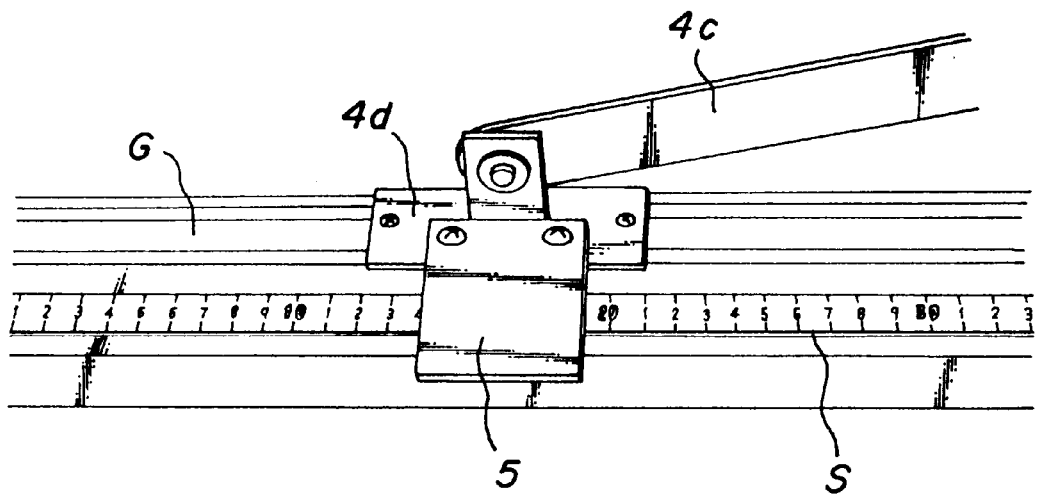

Subsequently, as shown in FIG. 6, the table top member 4a is pushed forward gently, with the ankles assuming a natural state while both elbows are stretched. When the table 4 has been pushed out to the furthest point, the hands of the subject are removed from the table 4. The distance between the initial position and the furthest point of the table 4, which the table 4 has moved together with the cursor 5, is then measured. This measurement is carried out by reading the final position of the cursor 5 along the scale S, as shown in FIG. 7b.

Figure 8:
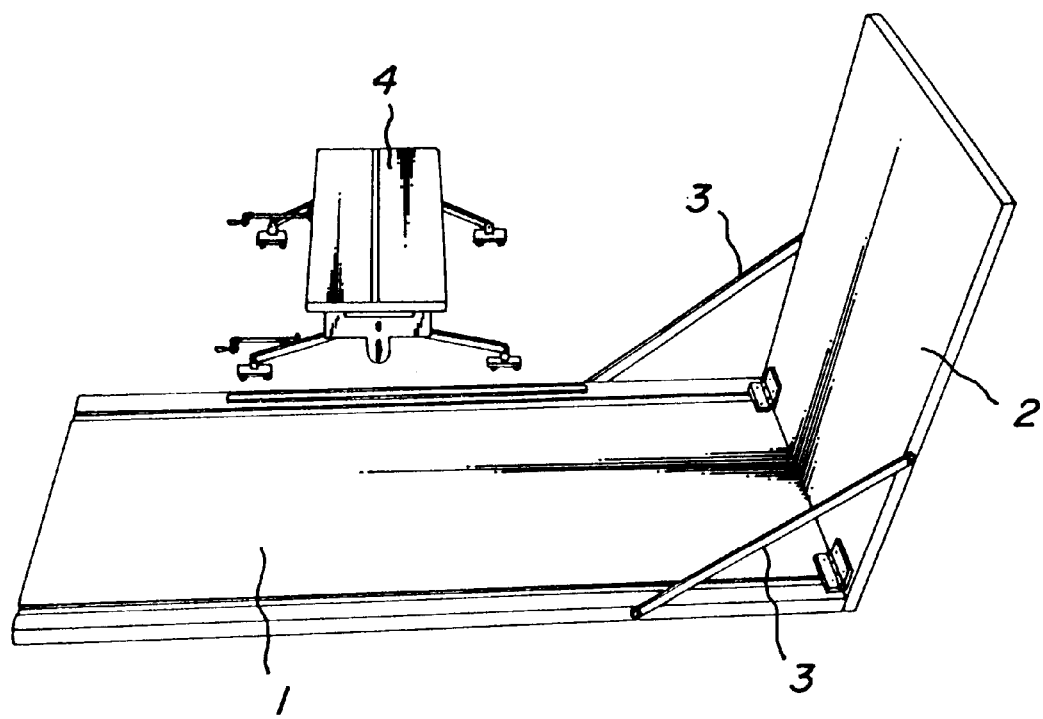
FIG. 8 is a view showing a state during removal of the table from the base plate.
Figure 9:
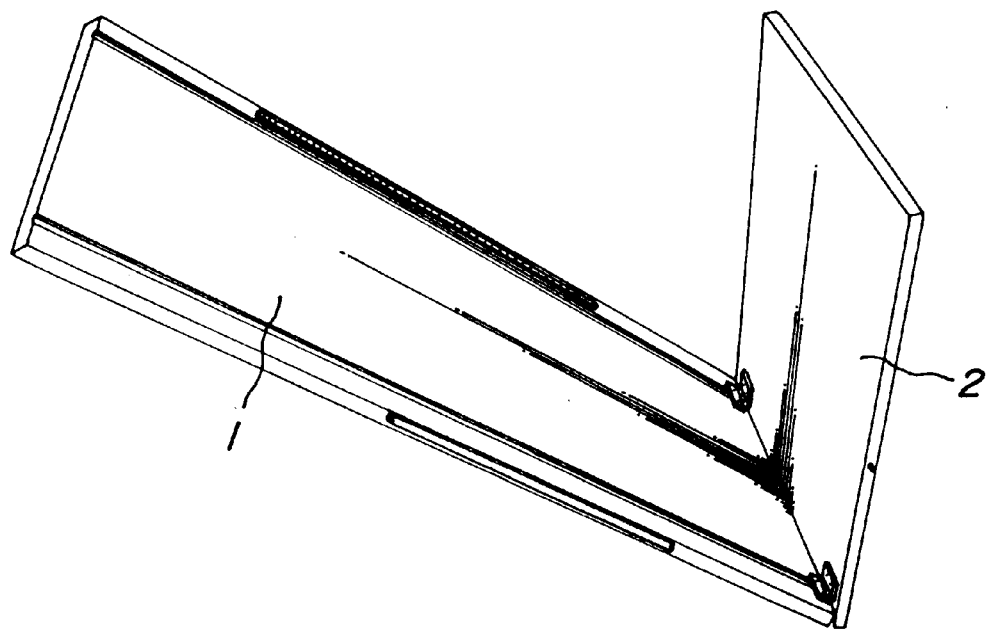
FIG. 9 is a view showing a state in which the back plate is folded over the base plate.

As mentioned above, the back plate 2 of the device in the illustrated embodiment of the present invention is pivotally connected to the base plate 1. Thus, after removing the stays 3 and the table 4 from the device, as shown in FIG. 8, the back plate 2 can be folded over the base plate 1 as shown in FIG. 9. The device in such a folded state of the back plate 2 is convenient to carry and store, and requires less storage space.

Evaluation test has been performed to ascertain the utility of the measuring device according to the present invention. More particularly, the body anteflexion was measured with respect to a panel of 53 people (male and female subjects) at the age ranging from 18 years old to 52 years old, by using the device according to the present invention and the conventional devices for the standing-posture body anteflexion and the sitting-posture body anteflexion, and the mean values and the standard deviations of the body anteflexion were investigated.

As a result, it has been revealed that the mean value of the standing-posture body anteflexion was 12.1±6.3 cm, the mean value of the conventional sitting-posture body anteflexion by the Well's method was 12.1±7.2 cm, and the mean value of the conventional sitting-posture body anteflexion by the Werner/Minkler method was 36.2±7.1 cm. In contrast to the above, the mean value of the body anteflexion as measured by the device according to the present invention was 38.8±7.6 cm when the ankles of the subjects were fixed, and 40.7±7.2 when the ankles were unrestrained.

Furthermore, with respect to device according to the present invention, irrespective of whether the ankles of the subjects are fixed or unrestrained, it has been confirmed that there is a statistically significant correlation of r=0.80 to 0.82 with the standing-posture body anteflexion, r=0.76 to 0.77 with the conventional sitting-posture body anteflexion by Wells method, and r=0.83 with the conventional sitting-posture body anteflexion by Werner-Minkler method.

As for the impression in terms of easiness of use of the measuring devices, it has been confirmed that preference was given to the device according to the present invention by 35 people (67.3% of the panel), and to the conventional device by 13 people (25% of the panel), while 4 people (7.7% of the panel) answered "tossup". Also, in terms of whether the ankles are fixed or unrestrained, preference was given to "ankles free" by 37 people (70.6% of the panel), and to "ankles fixed" 12 people (23.5% of the panel), while 3 people (5.9% of the panel) answered "tossup". It is thus clear that, when the device according to the present invention is used, the measurement should be made with the ankles of the subjects being unrestrained.

It will be appreciated from the foregoing description that, according to the present invention, the measurement of the sitting-posture body anteflexion can be performed with the ankles of the subject unrestrained, the subject is essentially free from physical pain which would otherwise be caused by stretching the muscles and tendons on the back side of the knee. Thus, the measuring device can be easily and safely used for the people of wide age group, without undue physical burden. Also, the measurement is performed with the hands of the subject maintained at an interval of the breadth of shoulders, so that the shoulders allow the flexibility of the waist to be fully demonstrated. Moreover, since hands of the subject are placed on, and supported by the table, part of the body weight is supported and the body anteflexion motion can be performed without uneasiness.

While the present invention has been described above with is reference to a specific embodiment, it has been presented by way of example only. It is of course that various changes and modifications may be made without departing from the scope of the invention as defined by the appended claims.

I claim:

1. A sitting-posture body anteflexion measuring device, comprising:

a base plate provided with a scale for measuring a body anteflexion of a subject, said scale extending in a longitudinal direction of the base plate and having a predetermined reference point;

a back plate having a lower end connected to one end of said base plate, said back plate being capable of assuming an upright posture relative to the base plate; and a table which is movable in the longitudinal direction of the base plate toward and away from the back plate, said table having a cursor which is movable along the scale for reading the movement distance of the cursor as measured from said reference point.

2. The device according to claim 1, further comprising side stays for retaining the back plate in the upright posture relative to the base plate.

3. The device according to claim 1, wherein the back plate is pivotally connected to the base plate so that it can be folded over the base plate.

4. The device according to claim 1, wherein said table comprises a table top member, a plurality of legs connected to the table top member, and means for adjusting the height of said table top member relative to said base plate.

5. The device according to claim 4, wherein said table comprises a plurality of legs which are pivotally connected to the table top member.

6. The device according to claim 5, wherein said base plate has a pair of longitudinal guide tracks along both side edges of the base plate, said legs of the table each having a caster which can be guided by relevant one of the guide tracks.

* * * * *